United States Patent
Barnett

(10) Patent No.: US 9,199,060 B1
(45) Date of Patent: *Dec. 1, 2015

(54) NON-BLADDER INVASIVE URETHRAL CATHETER SYSTEM

(71) Applicant: Henry Allison Barnett, Pike Road, AL (US)

(72) Inventor: Henry Allison Barnett, Pike Road, AL (US)

(*) Notice: Subject to any disclaimer, the term of this patent is extended or adjusted under 35 U.S.C. 154(b) by 32 days.

This patent is subject to a terminal disclaimer.

(21) Appl. No.: 14/474,104

(22) Filed: Aug. 30, 2014

Related U.S. Application Data

(63) Continuation-in-part of application No. 13/926,040, filed on Jun. 25, 2013, now Pat. No. 8,827,985.

(51) Int. Cl.
*A61M 25/00* (2006.01)
*A61M 27/00* (2006.01)

(52) U.S. Cl.
CPC .......... *A61M 25/0017* (2013.01); *A61M 27/00* (2013.01)

(58) Field of Classification Search
CPC ... A61M 27/00; A61M 1/00; A61M 25/0017; A61M 25/002; A61M 25/0111; A61M 25/007; A61M 25/00; A61F 5/44
USPC ........... 604/544, 541, 19, 317, 99.04, 103.03, 604/101.01
See application file for complete search history.

(56) References Cited

U.S. PATENT DOCUMENTS

| | | | |
|---|---|---|---|
| 3,543,759 A | 12/1970 | McWhorter | |
| 3,811,450 A * | 5/1974 | Lord | 604/102.03 |
| 4,932,938 A | 6/1990 | Goldberg et al. | |
| 6,119,697 A | 9/2000 | Engel et al. | |
| 6,972,040 B2 | 12/2005 | Rioux et al. | |
| 8,500,684 B2 | 8/2013 | Gardner et al. | |
| 2005/0107771 A1 | 5/2005 | Finkbeiner | |
| 2008/0051762 A1* | 2/2008 | Tsukada et al. | 604/544 |
| 2009/0315684 A1* | 12/2009 | Sacco et al. | 340/10.6 |

FOREIGN PATENT DOCUMENTS

GB 2235383 6/1991
WO WO 2009152609 A1 * 12/2009 ............ A61M 25/04

* cited by examiner

*Primary Examiner* — Philip R Wiest
*Assistant Examiner* — Benjamin Klein
(74) *Attorney, Agent, or Firm* — Gerald M. Walsh; Leo Law Firm, LLC

(57) ABSTRACT

A non-bladder invasive urethral catheter system with a urethral balloon element for relieving urinary incontinence. The catheter system is more convenient and less intrusive compared to bladder catheters and permits the catheter to remain in the urethra during urination. The catheter system blocks urine flow and leakage in the urethra by means of the urethral balloon element while inserted within the urethra. Two or more different urethral catheters are utilized that are differentiated by the positioning of a urethral balloon element on the elongated body of the urethral catheter. Through the placement of the urethral balloon element in different positions in the urethra with the different catheters, the trauma produced by a urethral balloon element to a particular area of the urethra is reduced or eliminated, allowing long term use of a catheter in the urethra.

10 Claims, 9 Drawing Sheets

NON-BLADDER INVASIVE URETHRAL CATHETER SYSTEM

The current application claims priority to U.S. Provisional Patent Application Ser. No. 61/771,231 filed on Mar. 1, 2013 and to U.S. Nonprovisional patent application Ser. No. 13/926,040 filed Jun. 25, 2013.

FIELD OF THE INVENTION

The present invention relates generally to a system of catheters, more particularly to a system of non-bladder invasive catheters that are positioned within the user's urethra to help relieve urinary incontinence and stenosis issues while reducing localized irritation to the walls of the urethra.

BACKGROUND OF THE INVENTION

Urinary incontinence is the involuntary leakage of urine. This condition has a number causes, including urethral strictures, bladder spasms, damaged muscles or nerves, an overactive bladder, prostate surgery, birth defects, polyuria, an enlarged prostate, radiation or drug treatments to the prostate, multiple sclerosis, spina bifida, Parkinson's disease, stroke, spinal cord injury, old age, and many other diseases and injuries. Millions of individuals must deal with this problem on a daily basis. Although, methods, devices, and systems are provided in various prior art, many of these existing solutions are unable to address the condition of urinary incontinence in a manner that does not incur additional pain, discomfort, and inconvenience to the user.

SUMMARY OF THE INVENTION

The present invention provides a system of different non-bladder invasive urethral catheters. A catheter is positioned within a user's urethra to help relieve urinary incontinence while minimizing localized irritation to the walls of the urethra. The catheter system provides a convenient and minimally intrusive means for enabling individuals suffering from urinary incontinence to live an ordinary lifestyle. The catheter does not enter the bladder and can remain in the urethra during urination. A urethral balloon element on the catheter blocks urine flow or leakage in the urethra but allows urination through the catheter. This eliminates the need for a user to wear a diaper or a similar means of absorbing leakage. The non-bladder invasive urethral catheter system utilizes several urethral catheters that are differentiated by the positioning of a urethral balloon element on the elongated body of the catheter. Through the substitution of the different catheters trauma produced by a urethral balloon element to a particular area of the urethra is minimized or eliminated.

Urinary incontinence is prevented by inserting the urethral catheter into a urethra to position a urethral balloon element in the urethra. The urethral balloon element is inflated to channel urine flow through the urethral catheter and to prevent urine flow in the urethra. This allows urine to flow out of the urethral catheter when a drainage assembly is opened and prevents urine from flowing out of the urethral catheter when the drainage assembly is closed. After a desired period of time, the original urethral catheter is replaced with a different urethral catheter wherein a urethral balloon element in the different urethral catheter is in a different position in a central portion of the catheter, compared to the original urethral catheter, thereby positioning a urethral balloon element in a different position in the urethra compared to the original urethral catheter. This process of replacing one catheter with another is repeated as desired to minimize or eliminate trauma caused by a urethral balloon element to a particular area of the urethra.

DETAILED DESCRIPTION OF THE INVENTION

All illustrations of the drawings are for the purpose of describing selected versions of the present invention and are not intended to limit the scope of the present invention.

Figure 1:
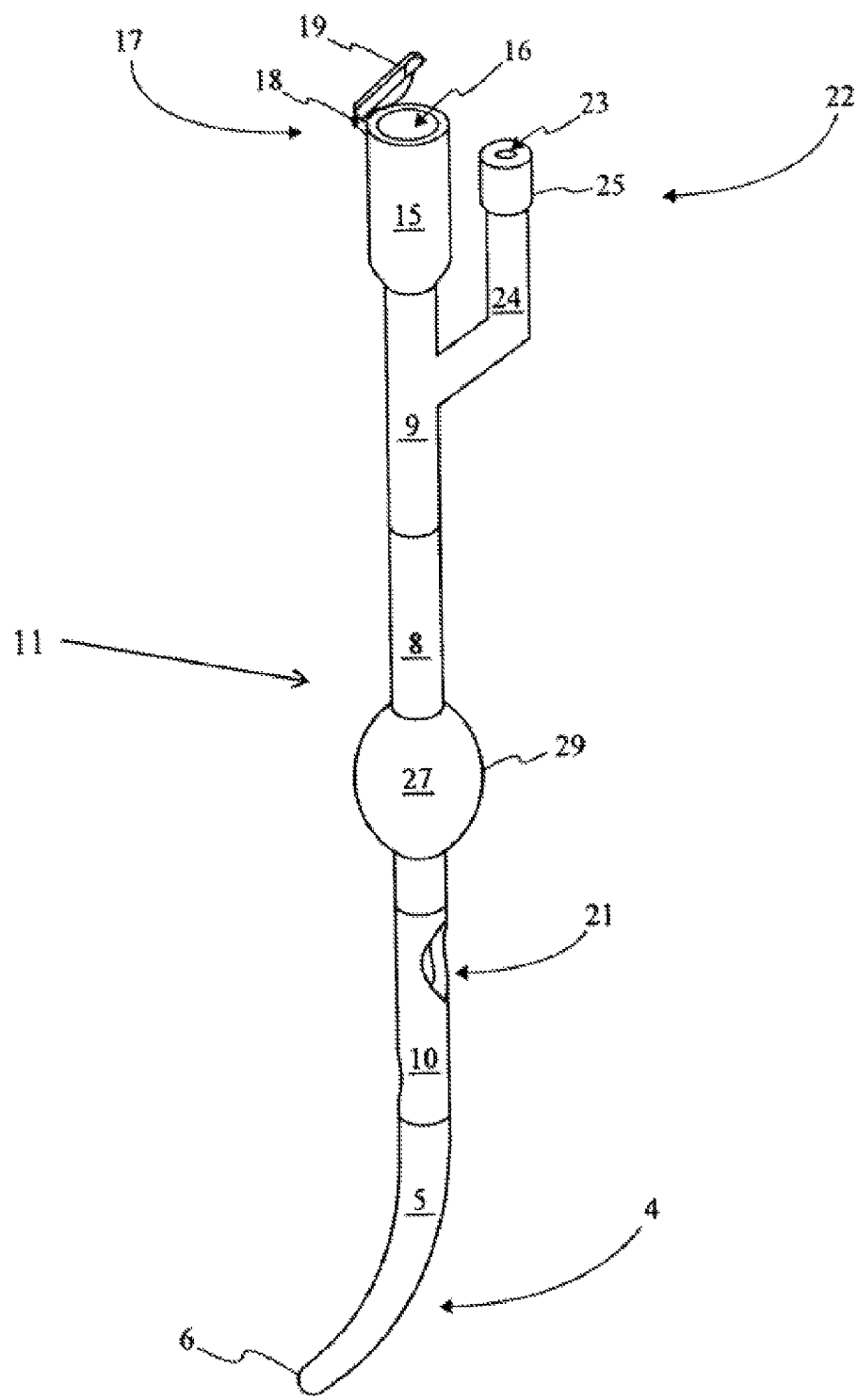
FIG. 1 is a front perspective view displaying the non-bladder invasive urethral catheter as per the current embodiment of the present invention.
Figure 2:
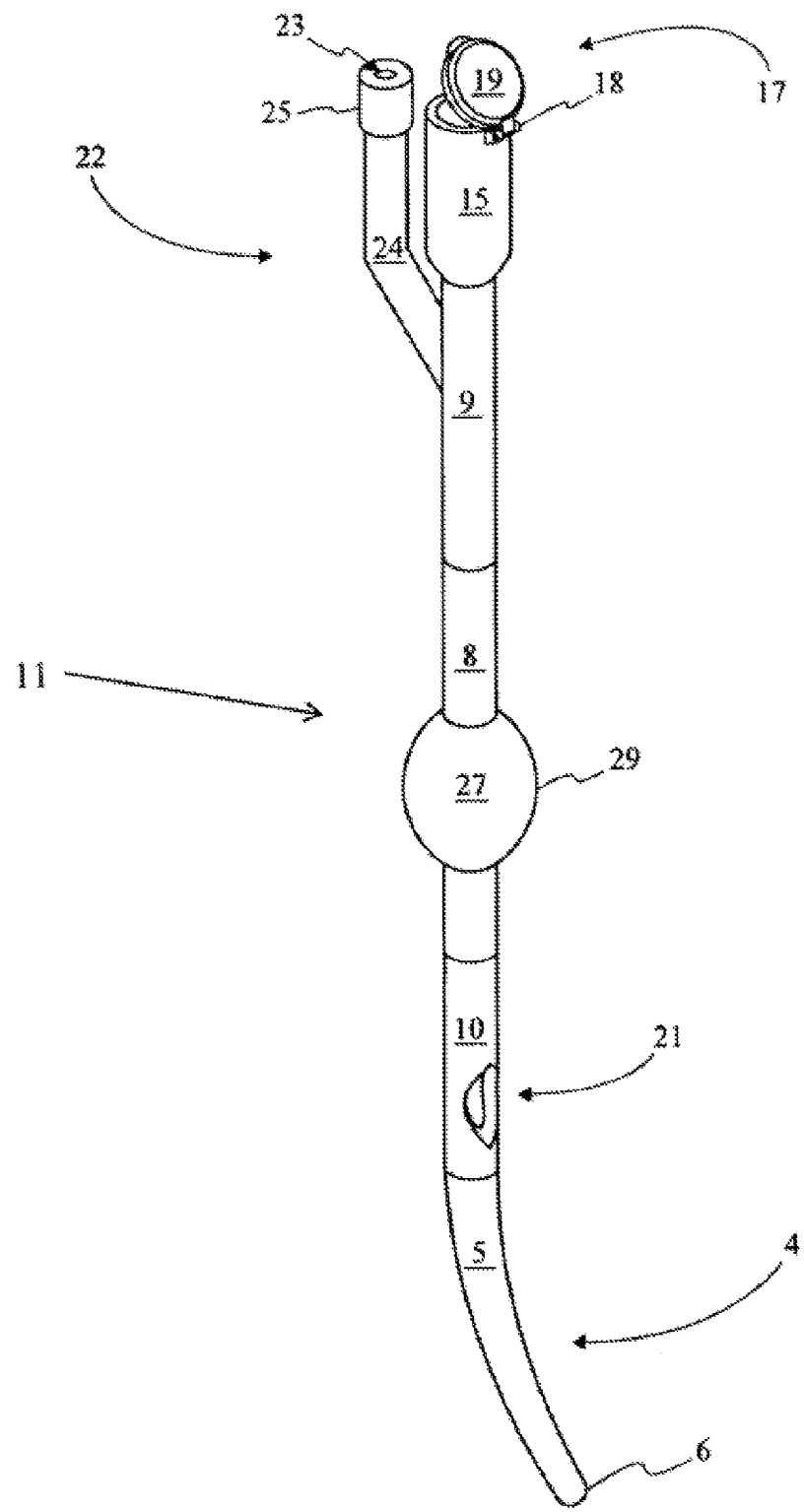
FIG. 2 is a rear perspective view displaying the non-bladder invasive urethral catheter as per the current embodiment of the present invention.
Figure 3:
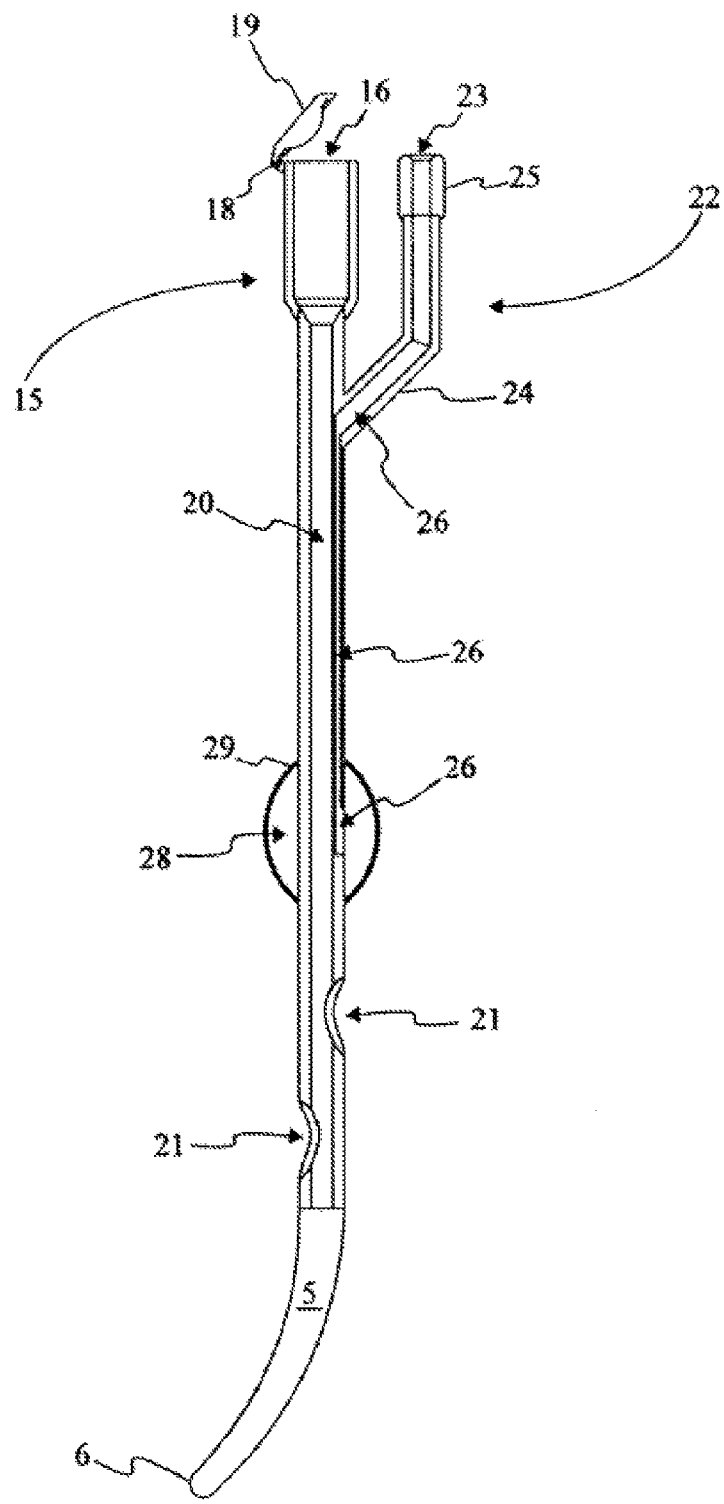
FIG. 3 is a cross sectional view displaying the non-bladder invasive urethral catheter as per the current embodiment of the present invention.

Referencing FIG. 1-FIG. 3, the present invention is a non-bladder invasive urethral catheter system that provides a user with a means of relieving urinary incontinence issues while reducing damage and injury caused to the urethra from localized pressure points associated with a urethral balloon element 27. In the current embodiment of the present invention, the non-bladder invasive urethral catheter system comprises a first urethral catheter 1, a second urethral catheter 2, and a third urethral catheter 3 (see FIGS. 5-7). The first urethral catheter 1, the second urethral catheter 2, and the third urethral catheter 3 each comprise an insertion tip 4, an elongated body 8, one or more urine inlets 21, a drainage lumen 20, a drainage assembly 15, an inflation assembly 22, an inflation lumen 26 and a urethral balloon element 27. The insertion tip 4 is a smooth rounded structure with a semi rigid construction that utilizes a particular curvature in order to guide the catheter through the urethra. The elongated body 8 is a cylindrical structure that is guided into the urethra by the insertion tip 4. The elongated body 8 is provided with a flexible construction and an appropriate diameter, relative to the user's urethra, in order to facilitate insertion and permit normal movement of the urethra with the indwelling catheter. The one or more urine inlets 21 are provided as fluid ducts that direct the user's urine into the catheter. The drainage lumen 20 is the provided as the fluid channel that transports the user's urine through the elongated body 8. The drainage assembly 15 is a terminal structure associated with the drainage lumen 20 that functions as the exhaust point for the user's urine. The inflation assembly 22 is a terminal structure associated with the inflation lumen 26 that permits fluid passage in order to inflate the urethral balloon element 27. The inflation lumen 26 is the fluid channel associated with fluid transport between the inflation assembly 22 and the urethral balloon element 27. The urethral balloon element 27 is the elastic structure that upon inflation permits the retention of the present invention within the user's urethra. The first urethral catheter 1, the second urethral catheter 2 and the third urethral catheter 3 contain similar component distribution but differ in the particular positioning of the urethral balloon element 27 relative to the elongated body 8. The shared component distribution allows the first urethral catheter 1, the second urethral catheter 2, and the third urethral catheter 3 to function as interchangeable components within the non-bladder invasive urethral catheter system.

Referencing FIG. 1-FIG. 3, the elongated body 8 is essential to the function of the present invention and is directly associated with the insertion tip 4, the one or more urine inlets 21, the drainage lumen 20, the drainage assembly 15, the inflation assembly 22, the inflation lumen 26, and the urethral balloon element 27. Both the drainage lumen 20 and the inflation lumen 26 are found positioned within the elongated body 8, wherein the elongated body 8 serves as the enclosure that houses both the drainage lumen 20 and the inflation lumen 26. The drainage lumen 20 traverses the length of the elongated body 8. The drainage lumen 20 is coincident with the drainage assembly 15 which is terminally positioned on the elongated body 8, opposite the one or more urine inlets. The one or more urine inlets 21 are also coincident with the drainage lumen 20 but are found peripherally positioned on the elongated body 8. The one or more urine inlets 21 are found positioned between the insertion tip 4 and the urethral balloon element 27. The one or more urine inlets 21 become coincident with the drainage lumen 20 by traversing the exterior portion of the elongated body 8. The coincident relation provided to the drainage assembly 15 and the one or more urine inlets 21 permit the drainage assembly 15 to be in fluid communication with the one or more urine inlets 21 by way of the drainage lumen 20. Additionally, the peripheral positioning of the one or more urine inlets 21 positions the one or more urine inlets 21 in a perpendicular arrangement to the drainage assembly 15, relative to the elongated body 8. The inflation assembly 22 is found positioned adjacent to the drainage assembly 15 but engaged peripherally to the elongated body 8. The inflation assembly 22 extends away from the exterior portion of the elongated body 8 forming an angled member. The inflation lumen 26 is positioned peripherally to the drainage lumen 20 within the elongated body 8. The inflation lumen 26 runs parallel to the drainage lumen 20 within the elongated body 8. The inflation lumen 26 is positioned between the inflation assembly 22 and the urethral balloon element 27. The urethral balloon element 27 is circumferentially positioned on the elongated body 8. The urethral balloon element 27 is positioned on the elongated body 8 between the one or more urine inlets 21 and the inflation assembly 22. The urethral balloon element 27 is coincident with inflation lumen 26. The coincident relation provided to the inflation assembly 22 and the urethral balloon element 27 permits the inflation assembly 22 to be in fluid communication with the urethral balloon element 27 by way of the inflation lumen 26.

Referencing FIG. 1 and FIG. 2, the elongated body 8 is a cylindrical structure that is provided with a flexible construction and an appropriate diameter, relative to the user's urethra, in order to facilitate insertion and permit normal movement of the urethra with the indwelling catheter. In the current embodiment of the present invention, the elongated body 8 comprises a distal end 9, a proximal end 10, and an inflation region 11. The distal end 9 represents the portion of the elongated body 8 that remains outside of the user's body while the proximal end 10 is the region that is found opposite but is positioned within the user's body. The distal end 9 is the region of the elongated body 8 that contains the drainage assembly 15 and the inflation assembly 22. The drainage assembly 15 is coupled to the terminal portion of the distal end 9 while the inflation assembly 22 is coupled to the peripheral portion of the distal end 9. The relation between the inflation assembly 22 and the distal end 9 provides the inflation assembly 22 as being extended away from the drainage assembly 15. The proximal end 10 serves as the attachment point for the one or more urine inlets 21 and the insertion tip 4. The insertion tip 4 is coupled to the terminal portion of the proximal end 10, wherein the engagement between the proximal end 10 and the insertion tip 4 seals the drainage lumen 20 allowing the one or more urine inlets 21 to function as the only means of fluid conveyance through the elongated body 8. Each of the one or more urine inlets 21 are peripherally positioned on the proximal end 10. The one or more urine inlets 21 are distributed equidistantly from each other on the proximal end 10. The one or more urine inlets 21 are found evenly spaced about the circumference of the proximal end 10, wherein the radian measurement between each of the one or more urine inlets 21 are congruent. The inflation region 11 is positioned between the proximal end 10 and the distal end 9. The inflation region 11 functions as the mounting point for the urethral balloon element 27. The inflation region 11 represents the region of the elongated body 8 where the positioning of the urethral balloon element 27 coincides with the user's urethra. The inflation region 11 provides a coincident relationship between the urethral balloon element 27 and the inflation lumen 26.

Referencing FIG. 1 and FIG. 2, the insertion tip 4, in the current embodiment of the present invention is provided as a semi rigid structure that guides the elongated body 8 into the user's urethra. The insertion tip 4 is found terminally positioned on the elongated body 8 opposite the positioning of the drainage assembly 15 and the inflation assembly 22. The insertion tip 4 is positioned adjacent to the one or more urine inlets 21 opposite the urethral balloon element 27. The insertion tip 4 is coupled to the terminal portion of the proximal end 10. In the current embodiment of the present invention, the insertion tip 4 comprises a curved tapered body 5 and a rounded end 6. The curved tapered body 5 provides facilitated insertion and catheterization of the present invention by reducing resistance during the insertion process. The curvature of the curved tapered body 5 coincides with the curvatures of the user's urethra, reducing discomfort felt by the user. The rounded end 6 functions as the blunt end of the curved tapered body 5 that evenly distributes pressure to the urethra around the curved tapered body 5 during insertion. The rounded end 6 is found terminally positioned on the curved tapered body 5 opposite the opposite the proximal end 10.

Figure 8:
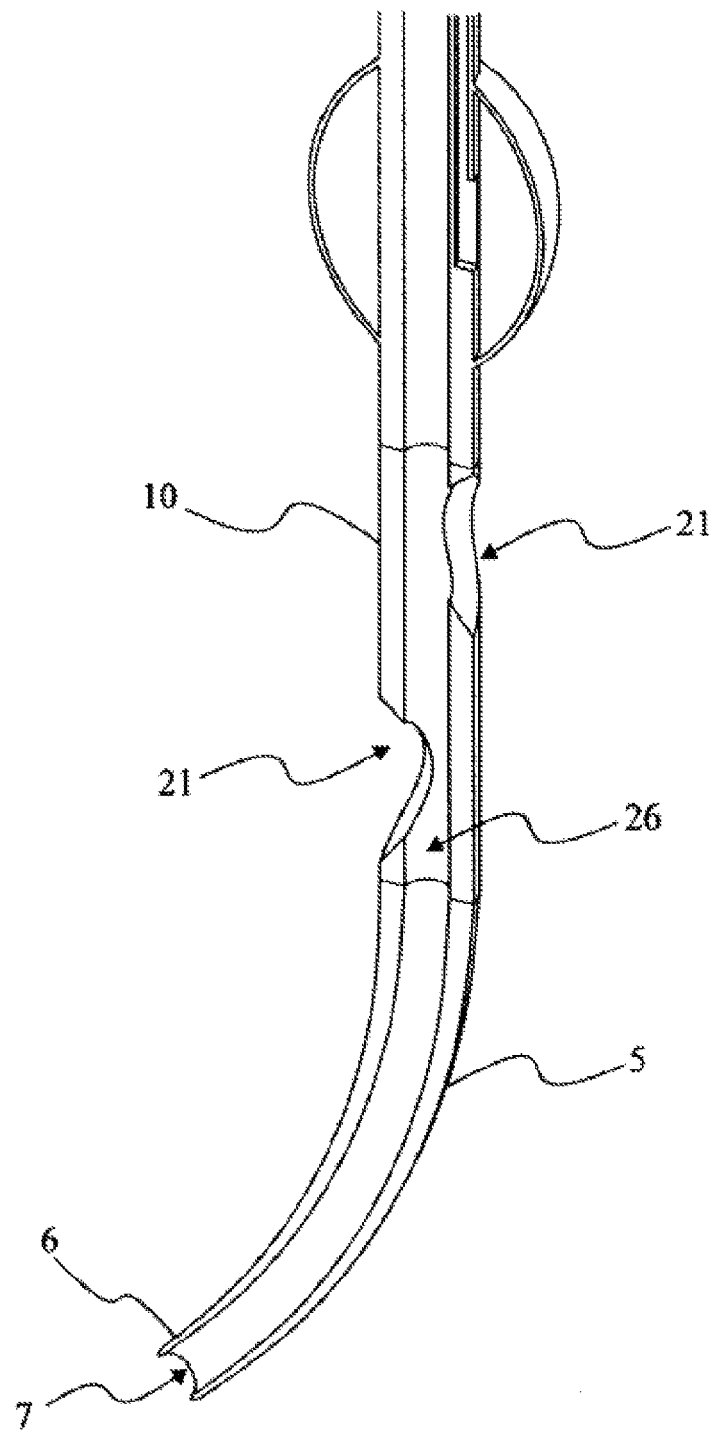
FIG. 8 is an enhanced cross sectional view displaying the insertion tip, the proximal end, and the inflation region as per the additional embodiment of the present invention.

Referencing FIG. 8, in an additional embodiment of the present invention, the insertion tip comprises an end channel 7. The end channel 7 functions as an extension of the drainage lumen 20 that allows a more direct avenue of fluid movement through the present invention. The end channel 7 is found positioned within the insertion tip 4 and traverses through the rounded end 6 and the curved tapered body 5. The end channel 7 is coincident with the drainage lumen 20 forming a conduit that spans the length of the present invention and terminates at the drainage assembly 15. It should be noted that the end channel 7 can be used in conjunction with the one or more urine inlets 21 as a means of improving fluid conveyance through the drainage lumen 20.

Figure 4:
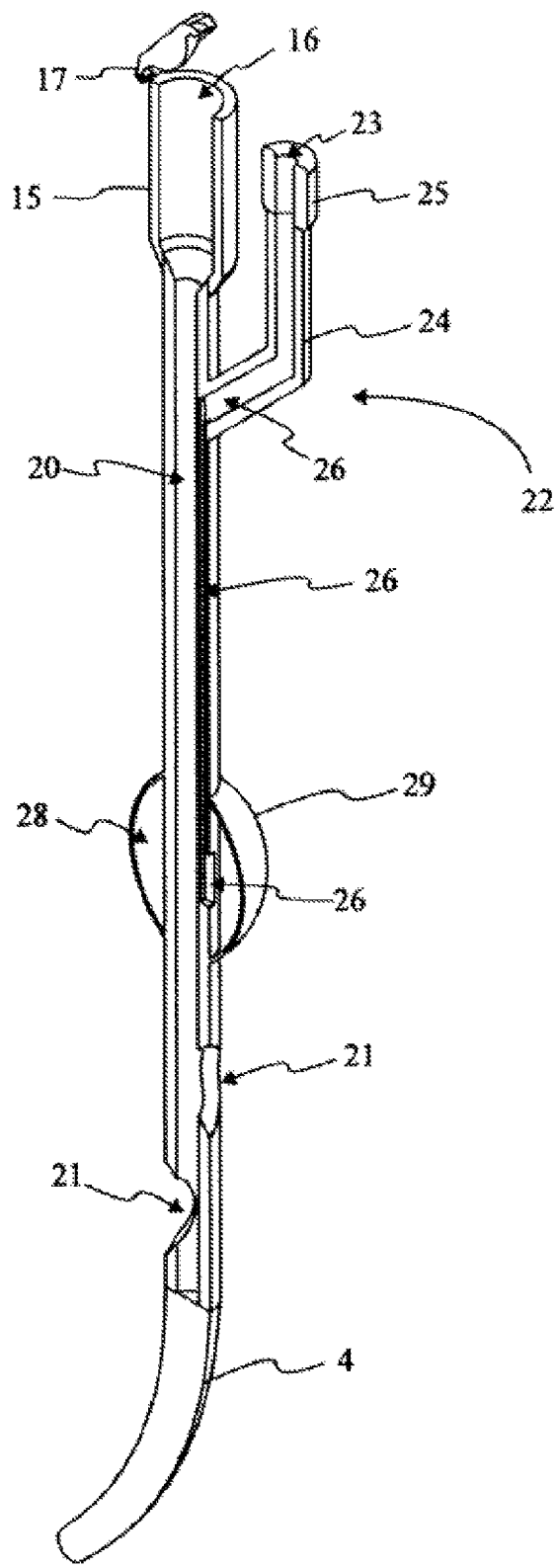
FIG. 4 is a cross sectional perspective view displaying the non-bladder invasive urethral catheter as per the current embodiment of the present invention.

Referencing FIG. 3 and FIG. 4, the one or more urine inlets 21 are provided as the apertures that permit fluid conveyance through the drainage lumen 20. Each of the one or more urine inlets 21 are peripherally positioned on the proximal end 10. The one or more urine inlets 21 are distributed equidistantly from each other on the proximal end 10. The one or more urine inlets 21 are found evenly spaced about the circumference of the proximal end 10, wherein the radian distance between each of the one or more urine inlets 21 neighboring each other is equal. It should be noted that while the current embodiment of the present invention is described as utilizing one or more urine inlets 21 that additional embodiments of the present invention may be configured to incorporate a singular urine inlet as well as accommodate as many urine inlets as needed. The drainage lumen 20 is provided as the fluid channel that transports the user's urine through the elongated body 8. The drainage lumen 20 is positioned within the elongated body 8 and extends from the proximal end 10 to the distal end 9. The drainage lumen 20 is positioned between the drainage assembly 15 and the one or more urine inlets 21. The drainage lumen 20 allows the one or more urine inlets 21 to be in fluid communication with the drainage assembly 15.

Referencing FIG. 1 and FIG. 3, the drainage assembly 15 is the terminal structure associated with the drainage lumen 20 that functions as the exhaust point for the user's urine. The drainage assembly 15 is in fluid communication with the one or more urine inlets 21 by way of the drainage lumen 20. The drainage assembly 15 is terminally positioned on distal end 9 of the elongated body 8. In the current embodiment of the present invention, the drainage assembly 15 comprises a drainage port 16 and a fluid impedance assembly 17. The drainage port 16 is the portion of the drainage assembly 15 that is coincident with the drainage lumen 20. The drainage port 16 allows the user's urine exit the present invention. The fluid impedance assembly 17 is the component structure that aligns with the drainage port 16 preventing the release of the users urine from the within the device. The fluid impedance assembly 17 is an essential component to the function of the present invention. The drainage assembly 15 can be provided in two embodiments that are differentiated by the engagement means of the fluid impedance assembly 17 to the drainage port 16. The first embodiment provides the fluid impedance assembly 17 as an integrated component with the drainage port 16 while the second embodiment provides the fluid impedance assembly 17 as a detachable element to the drainage port 16. The first embodiment of the drainage assembly 15 allows fluid impedance assembly 17 to function as an integrated valve that restricts flow through the drainage port 16. The second embodiment of the drainage assembly 15 allows the fluid impedance assembly 17 to function as any means of restricting or preventing fluid flow through the drainage port 16 that can be detached from the drainage port 16 if desired. In the preferred embodiment of the present invention, the fluid impedance assembly 17 comprises a hinge 18 and a stopper cap 19. The hinge 18 is peripherally positioned on the drainage port 16. The hinge 18 is provided with an engagement to the stopper cap 19 and the peripheral edge of the drainage port 16. The hinge 18 enables the stopper cap 19 to be pivotally coupled to the drainage port 16 allowing the stopper cap 19 to form an impermeable seal with the drainage port 16 when engaged.

Referencing FIG. 1 and FIG. 3, the inflation assembly 22 is a terminal structure associated with the inflation lumen 26 that permits fluid passage in order to inflate the urethral balloon element 27. The inflation assembly 22 is peripherally positioned to the drainage assembly 15. The inflation assembly 22 is in fluid communication with the urethral balloon element 27 by way to the inflation lumen 26. The inflation assembly 22 is found positioned adjacent to the drainage assembly 15 but engaged peripherally to the distal end 9 of the elongated body 8. The inflation assembly 22 extends away from the exterior portion of distal end 9 forming an angled member. In the current embodiment of the present invention, the inflation assembly 22 comprises an elongated base 24, an inflation valve 25, and an inflation port 23. The elongated base 24 allows the inflation assembly 22 to be extended away from the drainage assembly 15. The elongated base 24 is peripherally positioned to the distal end 9. The inflation lumen 26 traverses through the elongated base 24 in order to become coincident with the inflation valve 25. The inflation valve 25 is the fluid restricting element that prevents air/fluid from escaping the urethral balloon element 27 through the inflation lumen 26. The inflation valve 25 is positioned between the elongated base 24 and the inflation port 23. The inflation valve 25 is coincident with the inflation lumen 26 and provides the inflation port 23 with a means of fluid communication with the inflation lumen 26.

Referencing FIG. 3 and FIG. 4, the inflation lumen 26 is the fluid channel associated with fluid transport between the inflation assembly 22 and the urethral balloon element 27. The inflation lumen 26 is positioned between the urethral balloon element 27 and the inflation assembly 22. The inflation lumen 26 provides the inflation assembly 22 with a means of fluid communication with the urethral balloon element 27. The inflation lumen 26 is found positioned within the elongated body 8 but positioned peripherally to the drainage lumen 20. The inflation lumen 26 traverses the elongated body 8 from the inflation region 11 to the distal end 9. The inflation lumen 26 runs parallel to the drainage lumen 20 but diverts into the elongated base 24 of the inflation assembly 22 and ends coincident with the inflation region 11 of the elongated body 8.

Referencing FIG. 3 and FIG. 4, the urethral balloon element 27 is the elastic structure that upon inflation permits the retention of the present invention within the user's urethra. The urethral balloon element 27 is a bulb shaped fluid filled bladder. The urethral balloon element 27 is in fluid communication with the inflation assembly 22 by way of the inflation lumen 26. The urethral balloon element 27 is circumferentially positioned on the inflation region 11 of the elongated body 8, wherein the urethral balloon element 27 is concentric with the inflation region 11 of the elongated body 8. In the current embodiment of the present invention, the urethral balloon element 27 comprises an elastic exterior 29 and a fluid filled chamber. The elastic exterior 29 is the outer portion of the urethral balloon element 27 that becomes coincident with the user's urethra when inflated. The elastic exterior 29 hermetically encloses the fluid chamber 28 against the inflation region 11 of the elongated body 8. The fluid chamber 28 is in fluid communication with the inflation lumen 26.

Figure 5:
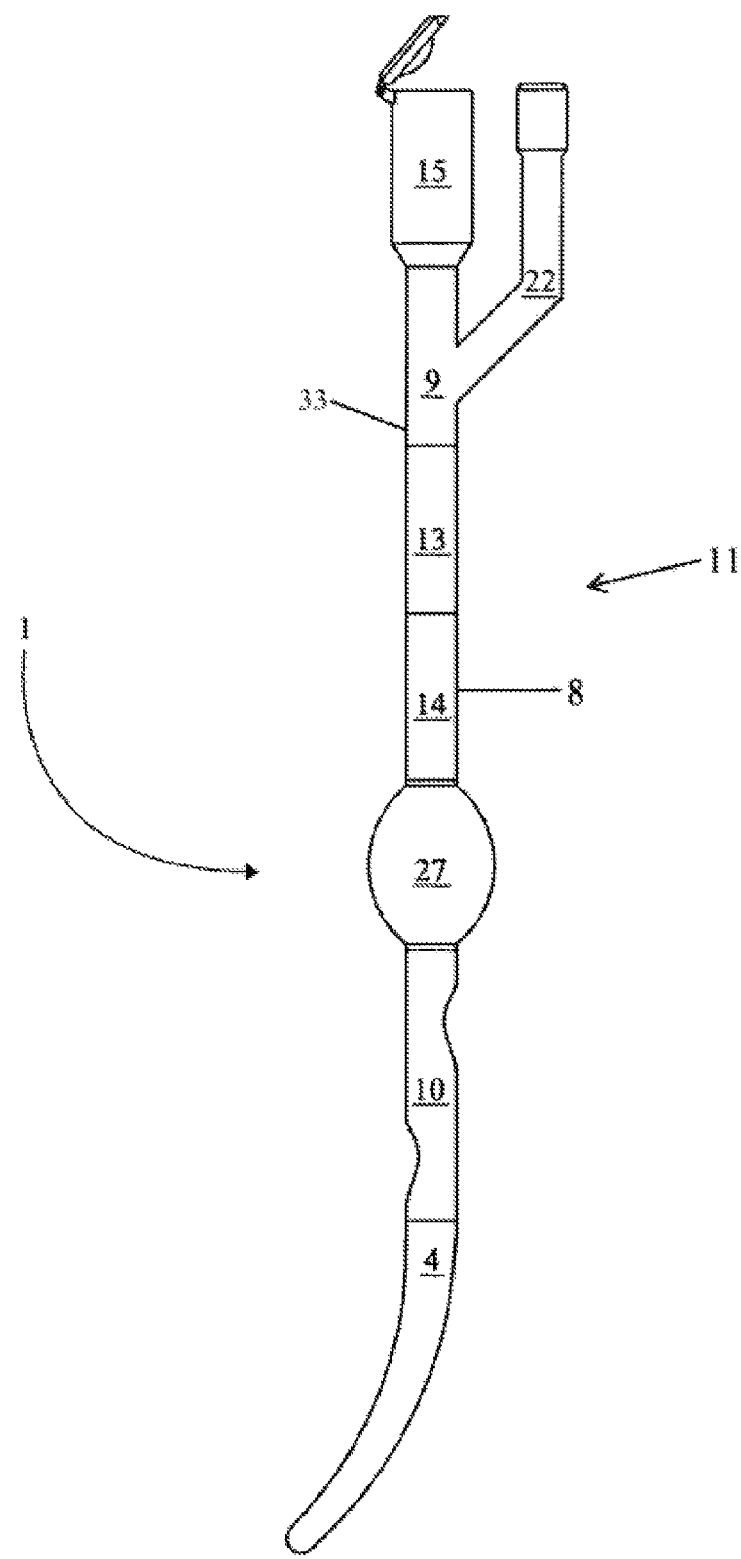
FIG. 5 is a front elevational view displaying the first urethral catheter configured as per the preferred embodiment of the present invention.
Figure 6:
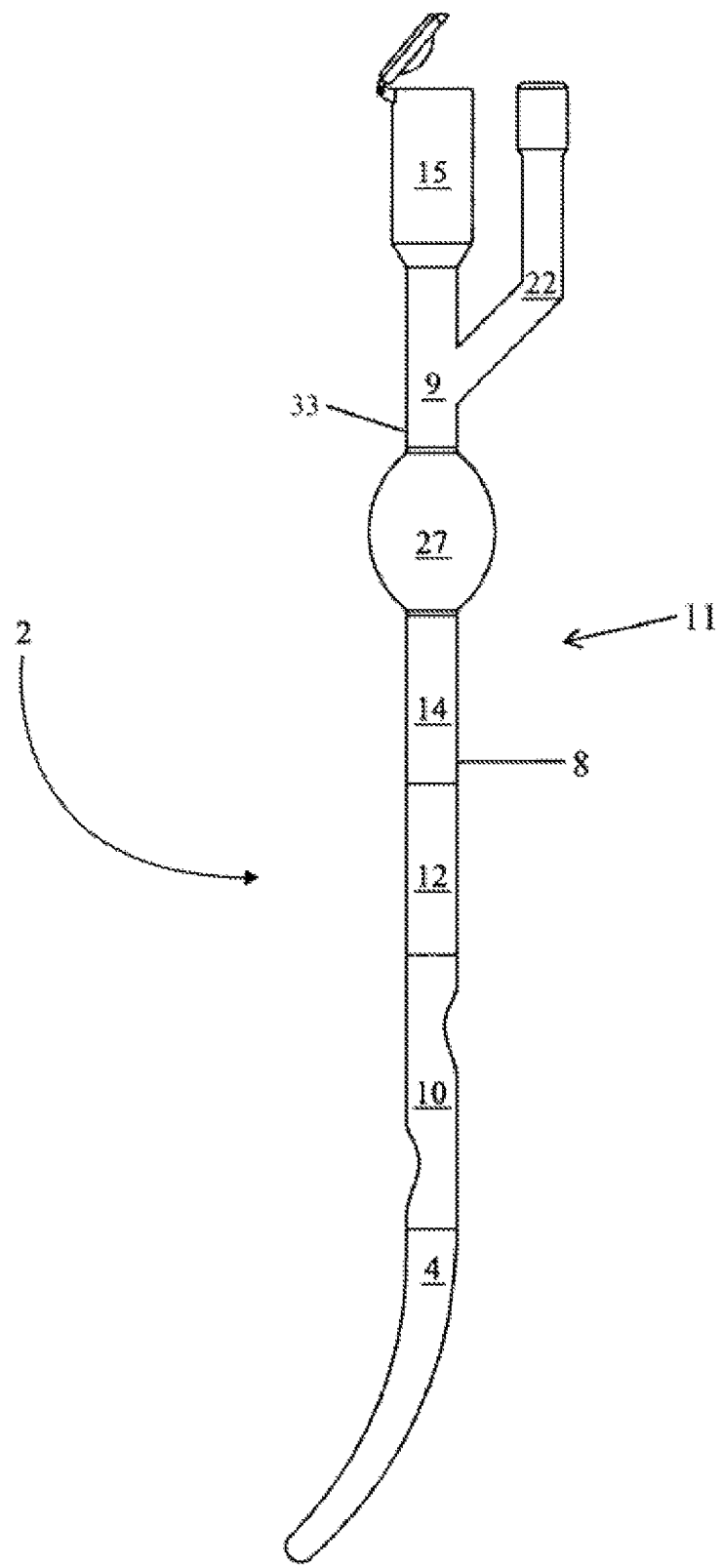
FIG. 6 is a front elevational view displaying the second urethral catheter configured as per the preferred embodiment of the present invention.
Figure 7:
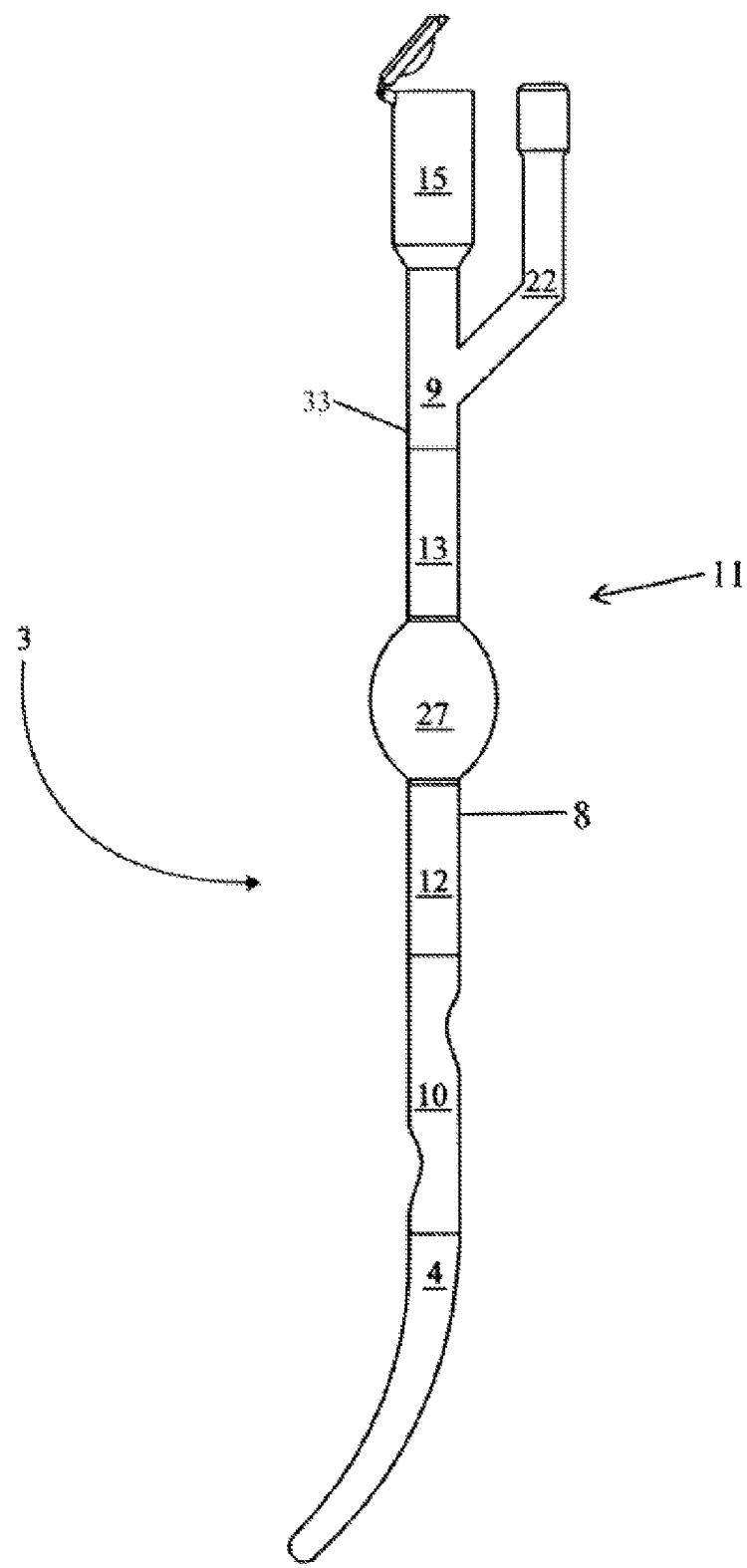
FIG. 7 is a front elevational view displaying the third urethral catheter configured as per the preferred embodiment of the present invention.

Referencing FIG. 5-FIG. 7, the inflation region 11 is the area of the elongated body 8 that contains the urethral balloon element 27. In the current embodiment of the present invention, the inflation region 11 comprises a first section 12, a second section 13, and a third section 14. The first section 12, the second section 13, and the third section 14, correspond to distinct areas of the inflation region 11 where the urethral balloon element 27 is mounted. The positioning of the urethral balloon element 27 on the first section 12, the second section 13, or the third section 14, differentiates the urethral catheter as being the first urethral catheter 1, the second urethral catheter 2 and the third urethral catheter 3. The first urethral catheter 1 contains the urethral balloon element 27 positioned coincident with the first section 12 of the inflation region 11. The second urethral catheter 2 contains the urethral balloon element 27 positioned coincident with the second section 13 of the inflation region 11. The third urethral catheter 3 contains the urethral balloon element 27 positioned coincident with the third section 14 of the inflation region 11. the distinction of between the first urethral catheter 1, the second urethral catheter 2 and the third urethral catheter 3 provides the system with a means of reducing the localized pressure to the urethra as a result of the positioning of the urethral balloon element 27.

Referencing FIG. 5-FIG. 7, in the preferred embodiment of the present invention, the non-bladder invasive urethral catheter system provides the present invention with a means of reducing localized pressure points within the user's urethra as a result of the urethral balloon element 27 positioning. The present invention accomplishes this through the interchangeable use of the first urethral catheter 1, the second urethral catheter 2 and the third urethral catheter 3. The user would utilize each of the non-bladder invasive catheters in similar manner. The user would stop using a particular catheter after a predetermined amount of time and then substitute it for another catheter. Due to the specific positioning of the urethral balloon element 27 on the inflation region 11, each catheter in the non-bladder invasive urethral catheter system would be coincident with a different section of the user's urethra. By alternating the use of each of the urethral catheters, the non-bladder invasive urethral catheter system would reduce localized compression associated with use of a urethral balloon catheter.

The current embodiment of the present invention has several advantages over incontinence devices disclosed in prior art. The present invention blocks urine flow or leakage until the user is ready to urinate, which in turn eliminates the need for a user to wear a diaper or a similar means of absorbing leakage. The present invention permits a user to urinate without having to remove and reinsert the indwelling catheter, which in turn eliminates or significantly reduces irritation, pain, discomfort, and infections, caused by frequent re-catheterization. This benefit also enables a user to travel without having to carry a large supply of catheters. A user may also participate in a large range of activities with the indwelling catheter such as swimming, and the catheter can additionally be removed as needed to allow for other activities such as sexual intercourse.

In the current embodiment of the present invention, the non-bladder invasive urethral catheter system is specifically designed to address male urinary incontinence and stenosis issues. The combination of the elongated body 8 and the insertion tip 4 are particularly sized in order to be inserted through the penile portion of a male user's urethra. In the current embodiment of the present invention the insertion tip 4 is specifically designed to traverse through the male user's urethra but is provided in a manner that prevents the insertion tip 4 from traversing into the bladder. The flexible nature of the elongated body 8 reduces irritation to the base of the user's urethra. During use, the inflated urethral balloon element 27 would form a seal within the user's urethra preventing urine from traversing around the elongated body 8. The user's urine would be directed into the drainage lumen 20 by the one or more urine inlets 21. Once in the drainage lumen 20 the urine would be prevented from being excreted by the drainage assembly 15. The engagement of the fluid impedance assembly 17 to the drainage port 16 would prevent urine flow out of the present invention until the user was ready to urinate. Although the present invention is specifically designed for use in male users, it should be noted that the component distribution allows configuration for use in female users. In this additional embodiment, the curvature of the curved tapered body 5 would be reduced to accommodate the more linear path of the female urethra. Both the insertion tip 4 and the elongated body 8 would be shortened in order to more adequately conform to the length of a female user's urethra. Furthermore, additional components may be included in order to provide a more secure means of retaining the present invention within female users. These additional components may utilize the inflation assembly 22, the inflation lumen 26, and/or the urethral balloon element 27 in order to provide a gender specific means of resolving urinary incontinence issues.

In the current embodiment of the present invention, the fluid impedance assembly 17 is described as having two engagement configurations with the drainage port 16, wherein the fluid impedance assembly 17 can be provided with a detachable coupling to the drainage port 16 or as an integrated component built into the drainage port 16. While the preferred embodiment of the present invention describes a pivoting stopper cap 19 that is coupled to the peripheral portion of the drainage port 16, additional embodiments may incorporate a different component system that would either detachably couple to the drainage port 16 or be provided as an integrated component that cooperatively functions with the drainage port 16. In an additional embodiment of the present invention where the fluid impedance assembly 17 is provided as an integrated component, the fluid impedance assembly 17 could be provided as a valve system that can include but is not limited to compression valves and twist valves.

This urethral catheter system provides a method for preventing urinary incontinence while producing little or no damage to the urethra. An initial urethral catheter, for example, urethral catheter 1, 2, or 3, is inserted into the urethra by inserting the insertion tip 4 into the opening of the urethra to position the urethral balloon element 27 in the urethra. The urethral catheter is inserted a fixed distance, for example, until the junction 33 of the drainage assembly 15 and the inflation assembly 22 (see FIGS. 5-7) engages the opening of the urethra. The urethral balloon element 27 is then inflated with fluid through the inflation assembly 22 sufficiently to occlude the urethra. The inflated urethral balloon element 27 channels urine flow through the urethral catheter and prevents urine flow through the urethra. Urine is allowed to flow out of the urethral catheter when the drainage assembly 15 is opened and is prevented from flowing out of the urethral catheter when the drainage assembly 15 is closed.

After a desired period of time, for example 1 hour to 10 days, the initial urethral catheter is replaced with a different urethral catheter in the urethra. The urethral balloon element 27 in this other different urethral catheter is in a different position in the central portion or inflation region 11 compared to the initial urethral catheter. For example, if the initial urethral catheter is urethral catheter 1 (FIG. 5), it would be replaced with urethral catheter 2 (FIG. 6) or urethral catheter 3 (FIG. 7). This would position the urethral balloon element 27 of the different urethral catheter (2 or 3) in a different position in the urethra compared to the initial urethral catheter (1). This process is repeated as desired, for example replacing catheter 1 with catheter 2 or 3, replacing catheter 2 with catheter 1 or 3, or replacing catheter 3 with catheter 1 or 2. This replacing of one urethral catheter with a different urethral catheter minimizes or prevents trauma caused by a urethral balloon element 27 to a particular area of the urethra.

This method can be utilized with two or more urethral catheters which are different from each other with regard to the position of the urethral balloon element 27 in the central portion 11 of the urethral catheter.

Figure 9:
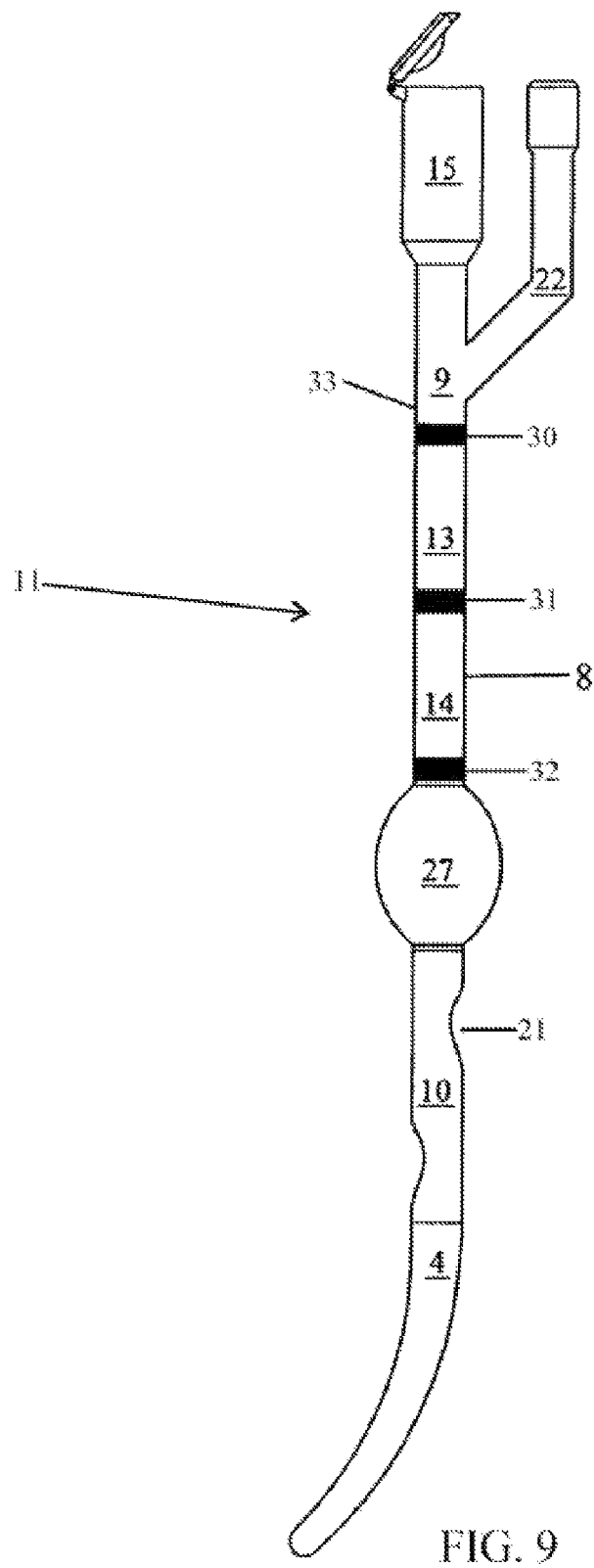
FIG. 9 shows an alternate embodiment of the urethral catheter illustrating position marks on the catheter for the placement of the urethral balloon element in different locations in the urethra.

FIG. 9 shows an alternate embodiment of the urethral catheter, illustrating position marks 30, 31, and 32 in a central portion of the elongated body 8 of the catheter. The position marks are for the placement of the urethral balloon element 27 in different locations in the urethra. The urethral balloon element 27 is positioned near the urine inlet 21 and between the urine inlet 21 and the distal end 9. The position marks are placed between the urethral balloon element 27 and the junction 33 of the drainage assembly 15 and the inflation assembly 22. The distance between the position marks is, preferably, the length of the urethral balloon element.

This alternant embodiment of the urethral catheter system also provides a method for preventing urinary incontinence while producing little or no damage to the urethra. A urethral catheter is inserted into the urethra by inserting the insertion tip 4 into the opening of the urethra to position the urethral balloon element 27 in the urethra. The urethral catheter is inserted an initial fixed distance, for example, until one of the position marks 30, 31, or 32 is positioned at the opening of the urethra. The urethral balloon element 27 is then inflated with fluid through the inflation assembly 22 sufficiently to occlude the urethra. The inflated urethral balloon element channels urine flow through the urethral catheter and prevents urine flow through the urethra. Urine is allowed to flow out of the urethral catheter when the drainage assembly 15 is opened and is prevented from flowing out of the urethral catheter when the drainage assembly 15 is closed.

After a desired period of time, for example 1 hour to 10 days, the urethral catheter is inserted further into or withdrawn from the urethra to a different position mark on the urethral catheter. At this different position mark the urethral balloon element 27 is in a different position in the urethra compared to the position of the initial position mark. For example, if the initial position mark is 30 (FIG. 9), it would be replaced with position mark 31 or 32 placed at the opening of the urethra. This would position the urethral balloon element 27 of the urethral catheter in a different position in the urethra compared to the position provided by placing position mark 30 at the opening of the urethra. This process is repeated as desired, for example replacing position mark 30 with position marks 31 or 32, replacing position mark 31 with position mark 30 or 32, or replacing position mark 32 with position mark 30 or 31. This replacing of one position mark at the opening of the urethra with a different position mark minimizes or prevents trauma caused by a urethral balloon element 27 to a particular area of the urethra. This method can be utilized with two or more position marks which are different from each other with regard to their distance from the urethral balloon element 27 in the central portion 11 of the urethral catheter.

Although the invention has been explained in relation to its preferred embodiments, it is to be understood that many other possible modifications and variations can be made without departing from the spirit and scope of the invention as hereinafter claimed. For example, although the fluid impedance assembly 17 is provided with a detachable engagement to the drainage port 16, the fluid impedance assembly 17 can be provided as a stopper or a seal that can include but is not limited to a screw on cap or stopper plug. The one or more urine inlets 21 can comprise a narrow end and a wide end. The narrow end and the wide end providing a particular tear drop shape that is able to more efficiently direct fluids into the drainage lumen 20. The tear drop shape may provide the narrow end oriented towards the proximal end 10 and the wide end oriented towards the distal end 9.

I claim:

1. A method of treating urinary incontinence, comprising:
 1) providing a urethral catheter system comprising:
    a) two or more urethral catheters, each having an elongated body with a drainage lumen and an inflation lumen, wherein said drainage lumen has one or more urine inlets and a drainage assembly, wherein said inflation lumen has a urethral balloon element and a balloon inflation assembly, and wherein said elongated body has an insertion tip;
    b) said elongated body having a distal end, a proximal end, and a central portion therebetween, wherein said drainage assembly and said balloon inflation assembly are near said distal end, said insertion tip and said one or more urine inlets are near said proximal end, and said urethral balloon element is circumferentially positioned on said central portion between said one or more urine inlets and said drainage assembly;
    c) said elongated body being constructed so that said insertion tip is prevented from entering the bladder when said urethral catheter is positioned in a urethra of a user;
    d) said urethral balloon element being inflated and deflated by means of said balloon inflation assembly, wherein, when said urethral balloon element is positioned in said urethra and is inflated, said urethral balloon element is constructed to form a seal within the user's urethra preventing urine from traversing around said elongated body, to cause urine to flow through said one or more urine inlets, and to cause said urethral catheter to remain in said urethra;
    e) said drainage assembly being constructed to allow urine to flow out of said urethral catheter when said drainage assembly is opened and to prevent urine from flowing out of said urethral catheter when said drainage assembly is closed; and
    f) each of said two or more urethral catheters being different from each other in that the position of said urethral balloon element on said central portion is different for each of said two or more urethral catheters so that each of said two or more urethral catheters has a urethral balloon element being coincident with a different section of said user's urethra compared to any of the other said two or more urethral catheters, wherein trauma to a particular area of said urethra, caused by said balloon element, is minimized by replacing one of said two or more urethral catheters with any of the other said two or more catheters;
 2) inserting said urethral catheter into a urethra to position said urethral balloon element in said urethra;
 3) inflating said urethral balloon element in said urethra to channel urine flow through said urethral catheter and to prevent urine flow in said urethra;
 4) allowing urine to flow out of said urethral catheter when said drainage assembly is opened and preventing urine from flowing out of said urethral catheter when said drainage assembly is closed;
 5) after a desired period of time, replacing said urethral catheter with a different urethral catheter in said urethra, wherein a urethral balloon element in said different urethral catheter is in a different position in said central portion compared to said urethral catheter, thereby positioning a urethral balloon element of said different urethral catheter in a different position in said urethra compared to said urethral catheter and 6) repeating steps 1) through 5) as desired, wherein, when replacing a urethral catheter with a different urethral catheter, trauma caused by a urethral balloon element to a particular area of said urethra is minimized.

2. The method of treating urinary incontinence of claim 1 wherein said insertion tip is tapered.

3. The method of treating urinary incontinence of claim 2 wherein, when said urethral balloon element is positioned in said urethra and is inflated, said urethral balloon element causes said urethral catheter to remain in said urethra during urination.

4. A method of treating urinary incontinence, comprising:
1) providing a urethral catheter comprising:
   a) a urethral catheter having an elongated body with a drainage lumen and an inflation lumen, wherein said drainage lumen has one or more urine inlets and a drainage assembly, wherein said inflation lumen has a urethral balloon element and a balloon inflation assembly, and wherein said elongated body has an insertion tip;
   b) said elongated body having a distal end, a proximal end, and central portion therebetween, wherein said drainage assembly and said balloon inflation assembly are near said distal end, said insertion tip and said one or more urine inlets are near said proximal end, and said urethral balloon element is circumferentially positioned on said central portion between said one or more urine inlets and said drainage assembly and near said one or more urine inlets;
   c) said elongated body being constructed so that said insertion tip is prevented from entering the bladder when said urethral catheter is positioned in a urethra of a user;
   d) said urethral balloon element being inflated and deflated by means of said balloon inflation assembly, wherein, when said urethral balloon element is positioned in said urethra and is inflated, said urethral balloon element is constructed to form a seal within the user's urethra preventing urine from traversing around said elongated body, to cause urine to flow through said one or more urine inlets, and to cause said urethral catheter to remain in said urethra;
   e) said drainage assembly being constructed to allow urine to flow out of said urethral catheter when said drainage assembly is opened and to prevent urine from flowing out of said urethral catheter when said drainage assembly is closed; and
   f) two or more position marks on said central portion between said urethral balloon element and said drainage assembly for placing said urethral balloon element in different locations in said urethra;
2) inserting said urethral catheter into a urethra and placing one of said position marks at an opening of said urethra to position said urethral balloon element in said urethra;
3) inflating said urethral balloon element in said urethra to channel urine flow through said urethral catheter and to prevent urine flow in said urethra;
4) allowing urine to flow out of said urethral catheter when said drainage assembly is opened and preventing urine from flowing out of said urethral catheter when said drainage assembly is closed;
5) after a desired period of time, placing a different position mark at an opening of said urethra to position said urethral balloon element in a different position in said urethra compared to that of said one of said position marks; and 6) repeating steps 1) through 5) as desired, wherein, when replacing one position mark with a different position mark on said urethral catheter at said opening of said urethra, trauma caused by a urethral balloon element to a particular area of said urethra is minimized.

5. The method of treating urinary incontinence of claim 4 wherein said insertion tip is tapered.

6. The method of treating urinary incontinence of claim 5 wherein, when said urethral balloon element is positioned in said urethra and is inflated, said urethral balloon element causes said urethral catheter to remain in said urethra during urination.

7. A method of treating urinary incontinence, comprising:
1) providing a urethral catheter system comprising:
   a) two or more urethral catheters, each having an elongated body with a drainage lumen and an inflation lumen, wherein said drainage lumen has one or more urine inlets and a drainage assembly, wherein said inflation lumen has a urethral balloon element and a balloon inflation assembly, and wherein said elongated body has an insertion tip;
   b) said elongated body having a distal end, a proximal end, and a central portion therebetween, wherein said drainage assembly and said balloon inflation assembly are near said distal end, said insertion tip and said one or more urine inlets are near said proximal end, and said urethral balloon element is circumferentially positioned on said central portion between said one or more urine inlets and said drainage assembly;
   c) said urethral balloon element constructed to remain in the urethra during use and to be inflated only in the urethra;
   d) said urethral balloon element being inflated and deflated by means of said balloon inflation assembly, wherein, when said urethral balloon element is positioned in said urethra and is inflated, said urethral balloon element is constructed to form a seal within the user's urethra preventing urine from traversing around said elongated body, to cause urine to flow through said one or more urine inlets, and to cause said urethral catheter to remain in said urethra;
   e) said drainage assembly being constructed to allow urine to flow out of said urethral catheter when said drainage assembly is opened and to prevent urine from flowing out of said urethral catheter when said drainage assembly is closed; and
   f) each of said two or more urethral catheters being different from each other in that the position of said urethral balloon element on said central portion is different for each of said two or more urethral catheters so that each of said two or more urethral catheters has a urethral balloon element being coincident with a different section of said user's urethra compared to any of the other said two or more urethral catheters, wherein trauma to a particular area of said urethra, caused by said balloon element, is minimized by replacing one of said two or more urethral catheters with any of the other said two or more catheters;
2) inserting said urethral catheter into a urethra to position said urethral balloon element in said urethra;
3) inflating said urethral balloon element in said urethra to channel urine flow through said urethral catheter and to prevent urine flow in said urethra;
4) allowing urine to flow out of said urethral catheter when said drainage assembly is opened and preventing urine from flowing out of said urethral catheter when said drainage assembly is closed; and 5) after a desired period of time, replacing said urethral catheter with a different urethral catheter in said urethra, wherein a urethral balloon element in said different urethral catheter is in a different position in said central portion compared to said urethral catheter, thereby positioning a urethral balloon element of said different urethral catheter in a different position in said urethra compared to said urethral catheter.

8. The method of treating urinary incontinence of claim 7 wherein said insertion tip is tapered and that when said urethral balloon element is positioned in said urethra and is inflated, said urethral balloon element causes said urethral catheter to remain in said urethra during urination.

9. A method of treating urinary incontinence, comprising:
1) providing a urethral catheter comprising:
   a) a urethral catheter having an elongated body with a drainage lumen and an inflation lumen, wherein said drainage lumen has one or more urine inlets and a drainage assembly, wherein said inflation lumen has a urethral balloon element and a balloon inflation assembly, and wherein said elongated body has an insertion tip;
   b) said elongated body having a distal end, a proximal end, and a central portion therebetween, wherein said drainage assembly and said balloon inflation assembly are near said distal end, said insertion tip and said one or more urine inlets are near said proximal end, and said urethral balloon element is circumferentially positioned on said central portion between said one or more urine inlets and said drainage assembly;
   c) said urethral balloon element constructed to remain in the urethra during use and to be inflated only in the urethra;
   d) said urethral balloon element being inflated and deflated by means of said balloon inflation assembly, wherein, when said urethral balloon element is positioned in said urethra and is inflated, said urethral balloon element is constructed to form a seal within the user's urethra preventing urine from traversing around said elongated body, to cause urine to flow through said one or more urine inlets, and to cause said urethral catheter to remain in said urethra; and
   e) said drainage assembly being constructed to allow urine to flow out of said urethral catheter when said drainage assembly is opened and to prevent urine from flowing out of said urethral catheter when said drainage assembly is closed, wherein said urethral catheter has one or more position marks on said central portion between said urethral balloon element and said drainage assembly;
2) inserting said urethral catheter into a urethra and placing one of said position marks at an opening of said urethra to position said urethral balloon element in said urethra;
3) inflating said urethral balloon element in said urethra to channel urine flow through said urethral catheter and to prevent urine flow in said urethra;
4) allowing urine to flow out of said urethral catheter when said drainage assembly is opened and preventing urine from flowing out of said urethral catheter when said drainage assembly is closed; and
5) after a desired period of time, placing a different position mark at an opening of said urethra to position said urethral balloon element in a different position in said urethra compared to that of said one of said position marks.

10. The method of treating urinary incontinence of claim 9 wherein said insertion tip is tapered and that when said urethral balloon element is positioned in said urethra and is inflated, said urethral balloon element causes said urethral catheter to remain in said urethra during urination.

* * * * *